US011602148B2

(12) United States Patent
Bristow

(10) Patent No.: US 11,602,148 B2
(45) Date of Patent: Mar. 14, 2023

(54) CRYSTALLINE FORM OF OXAMYL PROCESS FOR ITS PREPARATION AND USE OF THE SAME

(71) Applicant: JIANGSU ROTAM CHEMISTRY CO., LTD, Jiangsu (CN)

(72) Inventor: James Timothy Bristow, Chai Wan (HK)

(73) Assignee: JIANGSU ROTAM CHEMISTRY CO., LTD, Jiangsu (CN)

( * ) Notice: Subject to any disclaimer, the term of this patent is extended or adjusted under 35 U.S.C. 154(b) by 798 days.

(21) Appl. No.: 16/464,583

(22) PCT Filed: Oct. 20, 2017

(86) PCT No.: PCT/CN2017/107090
§ 371 (c)(1),
(2) Date: May 28, 2019

(87) PCT Pub. No.: WO2018/099203
PCT Pub. Date: Jun. 7, 2018

(65) Prior Publication Data
US 2021/0045384 A1    Feb. 18, 2021

(30) Foreign Application Priority Data
Nov. 29, 2016    (AU) ................. 2016265996

(51) Int. Cl.
*C07C 325/00*    (2006.01)
*A01N 37/52*    (2006.01)

(52) U.S. Cl.
CPC ............ *A01N 37/52* (2013.01); *C07C 325/00* (2013.01); *C07B 2200/13* (2013.01)

(58) Field of Classification Search
None
See application file for complete search history.

(56) References Cited

U.S. PATENT DOCUMENTS

| 3,506,698 | A |   | 4/1970  | Jelinek et al. |
|-----------|---|---|---------|----------------|
| 3,557,190 | A |   | 1/1971  | Buchanan |
| 3,584,032 | A |   | 6/1971  | Fuchs |
| 4,481,215 | A |   | 11/1984 | Tocker |
| 4,668,806 | A | * | 5/1987  | Mrowca ............... C07D 307/86 549/470 |
| 5,284,962 | A |   | 2/1994  | Rensi |
| 2015/0157017 | A1 |   | 6/2015 | Ikeda |
| 2016/0130229 | A1 |   | 5/2016 | Slomczynska et al. |

FOREIGN PATENT DOCUMENTS

| AU | 2016102051 A4 | 5/2017 |
| CN | 1086208 A | 5/1994 |
| EP | 0097464 A1 | 1/1984 |
| EP | 0200429 A2 | 5/1986 |
| WO | 2014201326 A1 | 12/2014 |

OTHER PUBLICATIONS

Haynes et al. (CRC Handbook of Chemistry and Physics, 94 Ed., 2014, Section 15) (Year: 2014).*
English translation of Zhu et al. (Journal of Taishan Medical College, vol. 27, No. 1, 2006) (Year: 2006).*
English translation of Guo et al. (Agrochemicals, vol. 42, Iss. 1, 2003, p. 11) (Year: 2003).*
AU Office Action for related Australian Patent Application No. AU2016265996 dated Nov. 17, 2017.
Chinese Office Action corresponding to Chinese Application No. 201780058252.1 dated Sep. 27, 2020.
Huiqin, Qi, The Research of the New Technology to Synthesis of Oxamylyl, Chemical Intermediate, Issue 11, Nov. 15, 2008, pp. 37-40.
Guo, Sheng, et al., Systhesis of Oxamyl, vol. 42, No. 1, Dec. 31, 2001, p. 11.
Zhu Xiao-hui, et al. Synthesis of New Type Pesticide Oxamyl, Journal of Taishan Medical College, vol. 27, No. 1, 2006.
International Search Report for corresponding International Application No. PCT/CN2017/107090 dated Jan. 15, 2018.
Written Opinion of the International Searching Authority for corresponding International Application No. PCT/CN2017/107090 dated Jan. 15, 2018.

* cited by examiner

*Primary Examiner* — Sudhakar Katakam
*Assistant Examiner* — Jennifer C Sawyer
(74) *Attorney, Agent, or Firm* — Dickinson Wright PLLC

(57) ABSTRACT

A crystalline form of oxamyl is provided. The crystalline form of oxamyl is of formula (I):

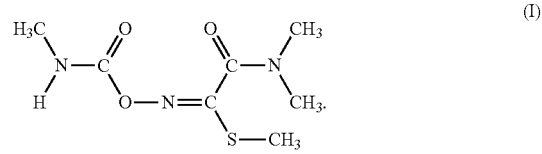

A crystal preparation process, the analyses of the crystal through various analytical methods, and using the crystalline form to prepare a stable agrochemical formulation is also provided. The use of various solvents towards the crystalline form preparation conditions is also provided.

25 Claims, 4 Drawing Sheets

CRYSTALLINE FORM OF OXAMYL PROCESS FOR ITS PREPARATION AND USE OF THE SAME

CROSS REFERENCE TO RELATED APPLICATIONS

This application is a 371 national phase entry of PCT/EP2017/107090, filed on 20 Oct. 2017, which claims priority to Australian Patent Application No. 2016265996, titled "A NOVEL CRYSTALLINE FORM OF OXAMYL, A PROCESS FOR ITS PREPARATION AND USE OF THE SAME", filed on Nov. 29, 2016, the entire contents of which are incorporated herein by reference.

FIELD

The present invention relates to a crystalline form of (EZ)-N,N-dimethyl-2-methylcarbamoyloxyimino-2-(methylthio)acetamide (oxamyl), to its preparation processes and to its use in agrochemical preparations.

BACKGROUND (EZ)-N,N-dimethyl-2-methylcarbamoyloxyimino-2-(methylthio)acetamide (oxamyl) is a potent insecticide/nematicide. Oxamyl has a molecular formula of $C_7H_{13}N_3O_3S$. Its chemical structure is:

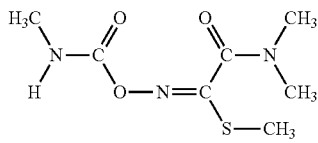

(I)

Oxamyl is a broad-spectrum carbamate insecticide/nematicide with many crop outlets, principally cotton and potato. It is also used on ornamentals, fruit trees, vegetables, cucurbits, beet, bananas, apples, carrots, celery, citrus, pineapples, peanuts, soy beans, tobacco and other crops for control of chewing and sucking insects (including soil insects, but not wireworms), spider mites, and nematodes. Oxamyl is now a mature product with relatively stable sales, due to registration of new uses and to EU Annex 1 re-registration.

The commercially available oxamyl, which is usually manufactured by the process described in U.S. Pat. No. 5,284,962, which is incorporated herein by reference for all purposes, is present in an amorphous state. However, it has been found that oxamyl in an amorphous state is not suitable for being prepared as compositions or formulations due to its high tendency to aggregate, in particular after prolonged storage. Therefore, there is a need to provide a novel form of oxamyl exhibiting improved properties, such as improved storage stability.

SUMMARY

In attempt to resolve some or all of the problems with existing amorphous form of oxamyl, a new and stable crystalline form of oxamyl has been prepared.

In a first aspect, the present invention provides a crystalline modification I of (EZ)-N,N-dimethyl-2-methylcarbamoyloxyimino-2-(methylthio)acetamide (oxamyl), termed "crystalline modification I", exhibiting at least three of the following reflexes, in any combination, as 2θ±0.20 degree in an X-ray powder diffractogram (X-RPD) recorded using Cu—Kα radiation at 25° C.:

| | |
|---|---|
| 2θ=12.72±0.20 | (1) |
| 2θ=16.17±0.20 | (2) |
| 2θ=16.60±0.20 | (3) |
| 2θ=17.71±0.20 | (4) |
| 2θ=19.26±0.20 | (5) |
| 2θ=20.03±0.20 | (6) |
| 2θ=21.04±0.20 | (7) |
| 2θ=22.87±0.20 | (8) |
| 2θ=24.43±0.20 | (9) |
| 2θ=25.04±0.20 | (10) |
| 2θ=25.57±0.20 | (11) |
| 2θ=26.16±0.20 | (12) |
| 2θ=26.88±0.20 | (13) |
| 2θ=29.63±0.20 | (14) |
| 2θ=29.91±0.20 | (15) |
| 2θ=31.14±0.20 | (16) |

In an embodiment, the crystalline modification I of oxamyl according to the first aspect of the invention, exhibiting at least 3, 4, 5, 6, 7, 8 or all of the following reflexes, in any combination, as 2θ±0.20 degree in an X-ray powder diffractogram recorded using Cu—Kα radiation at 25° C.:

| | |
|---|---|
| 2θ=12.72±0.2 | (1) |
| 2θ=16.17±0.2 | (2) |
| 2θ=16.60±0.2 | (3) |
| 2θ=19.26±0.2 | (5) |
| 2θ=21.04±0.2 | (7) |
| 2θ=22.87±0.2 | (8) |
| 2θ=25.04±0.2 | (10) |
| 2θ=25.57±0.2 | (11) |
| 2θ=31.14±0.2 | (16) |

In a second aspect, the present invention provides a crystalline modification I of oxamyl, optionally according to the first aspect of the invention, exhibiting an infrared (IR) with characteristic functional group vibration peaks at wavenumbers (cm$^{-1}$, ±0.2%) 3325, 2935, 2161, 1713 and 1659 cm$^{-1}$.

In a third aspect, the present invention provides a crystalline modification I of oxamyl, optionally according to the first or second aspect of the invention, exhibiting a melting point of 100° C. to 104° C., preferably 101° C. to 103° C., more preferably 102° C.

In a fourth aspect, the present invention provides a crystalline modification I of oxamyl, optionally according to any one of the first to third aspects of the invention, exhibiting a differential scanning calorimetry (DSC) profile having an endothermic melting peak at 102° C.

In a fifth aspect, the present invention provides a crystalline modification I of oxamyl, optionally according to any one of the first to fourth aspects of the invention, characterized by X-ray powder diffraction pattern substantially as shown in FIG. 2, and/or characterized by an IR spectrum substantially as shown in FIG. 1, and/or characterized by a DSC thermogram substantially as shown in FIG. 3.

In a sixth aspect, the present invention provides a crystalline modification I of oxamyl, optionally according to any one of the first to fifth aspects of the invention, obtainable by the process substantially as described in Example 2 or 3.

In a seventh aspect, the present invention provides a crystalline modification I of oxamyl, optionally according to any one of the first to sixth aspects of the invention, obtainable by the process of the eighth aspect of the invention.

It has been found that the crystalline modification I of oxamyl may show a significant improvement in its storage stability, which may significantly reduce the aggregation problem encountered with current commercially available formulations. In addition, it has been found that the crystalline modification I of oxamyl may exhibit a high degree of stability when formulated compared to amorphous oxamyl prepared in accordance with the disclosure of U.S. Pat. No. 5,284,962. In particular, the crystalline modification may exhibit a very low tendency to aggregate when formulated. This may allow the preparation of commercial formulations such as suspension concentrates (SC) and granules (GR)). Further, by virtue of good stability properties, the crystalline modification I of oxamyl may provide a desirable long storage period for formulations.

Methods for preparing amorphous oxamyl are well known in the art. Amorphous oxamyl is manufactured and available on a commercial scale. A particularly suitable method for preparing amorphous oxamyl is described in U.S. Pat. No. 5,284,962.

In an eighth aspect, the present invention provides a process for preparing a crystalline modification I of oxamyl comprising the steps of:
  i) dissolving oxamyl in a solvent or mixture of solvents;
  ii) precipitating the dissolved compound into crystalline modification I of oxamyl; and
  iii) isolating the precipitated crystalline modification I.

In an embodiment of the eighth aspect of the invention, the chlorfenapyr in step i) is amorphous oxamyl. In an embodiment of the eighth aspect of the invention, the solvent is selected from the group consisting of halogenated hydrocarbons (for example, trifluoro methyl benzene, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane, mesitylene), cymene, petroleum fractions having a boiling range of from 70° C. to 190° C., cyclohexane, methylcyclohexane, petroleum ether, ligroin, octane, toluene, xylene, esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), methyl ethyl ketone and aliphatic alcohols (for example, methanol, isopropyl alcohol, ethanol, n-propanol, isopropanol, n-butanol and tert-amyl alcohol) and mixtures thereof. Solvent mixtures of more than 2, or 3 or 4 components are also envisaged by embodiments of the invention.

In an embodiment of the eighth aspect of the invention, the solvent is selected from the group consisting of nitrobenzene, toluene, xylene, chlorobenzene, dichlorobenzene, trifluoro methyl benzene, mesitylene, ether, ethyl acetate or a mixture thereof.

In an embodiment of the eighth aspect of the invention, the solvent is selected from the group consisting of ethyl acetate and/or nitrobenzene or a mixture thereof.

In an embodiment of the eighth aspect of the invention, the concentrated homogeneous solution thus prepared as in step (i) is then cooled to room temperature or to a temperature of about 0° C. to 20° C. to crystallize the desired crystalline form from the solvent. The crystalline modification I of oxamyl can also be crystallized out by concentrating the homogeneous solution by removing the solvent or solvent mixture to a certain volume with or without applying vacuum and cooling to below the reflux temperature of the solvent or the solvent mixture.

In an embodiment of the eighth aspect of the invention, crystalline modification I of oxamyl can also be effected by adding seed crystals of the desired crystalline form during crystallization into a solution prepared in step (i), which can promote or accelerate the crystallization.

The seed crystal amount added to the concentrated solution is typically in the range of 0.001% to 10% by weight, optionally 0.001% to 2.5% by weight, further optionally 0.005 to 0.5% by weight based on the weight of oxamyl used for the preparation of concentrated solution in step (i). Optionally, the seed crystals are added to the concentrated solution at the temperature below the boiling point of the corresponding solvent or the solvent mixture.

In an embodiment of the eighth aspect of the invention, the precipitated crystalline modification I of oxamyl obtained from step (ii) is isolated by the usual solid component separation techniques from solutions, such as filtration, centrifugation or decantation. Then, the isolated solid is washed with solvent one or more times. Optionally, the solvent employed in the washing stage consists of one or more components of the solvent or solvent mixture employed for preparation of concentrated solution in step (i), as described hereinbefore. The washing is usually carried out using the corresponding solvent or solvent mixture between room temperature and 0° C., depending on the solubility of the crystal, in order to minimize or avoid the loss of crystalline material in the corresponding washing solvent as much as possible. In an embodiment of the eighth aspect of the invention, crystalline modification I of oxamyl is dissolved and recrystallized. The washings and/or the solvent of crystallization in any of the methods may be concentrated to obtain solid oxamyl which may be recycled.

In a ninth aspect, the invention provides a crystalline material comprising the crystalline modification I of oxamyl obtained according to the eighth aspect of the invention, having a content of a crystalline modification I of oxamyl content of at least 98% by weight.

In a tenth aspect, the present invention provides a composition comprising the crystalline modification I of oxamyl according to any one of the first to seventh and ninth aspects of the invention, and at least one auxiliary.

In an eleventh aspect, the present invention provides a use of the crystalline modification I of oxamyl according to any one of the first to seventh and ninth aspects of the invention, or a composition according to the tenth aspect of the invention for control of insects and nematodes.

In an embodiment of the tenth aspect of the invention, the amount of the crystalline modification I of oxamyl is less than 75% by weight of the composition, optionally less than 50% by weight of the composition. In an embodiment of the tenth aspect of the invention, the amount of the crystalline modification I of oxamyl is 42%. In an embodiment of the tenth aspect of the invention, the amount of the crystalline modification I of oxamyl is 24%. In an embodiment of the tenth aspect of the invention, the amount of the crystalline modification I of oxamyl is 10%.

The use of oxamyl as an insecticide and nematicide is well known in the art and is used on a commercial scale. It has been found that the crystalline modification I of oxamyl is also active in controlling insects and nematodes. As a result, the techniques of formulating and applying oxamyl known in the art with respect to amorphous oxamyl, for example as disclosed in the prior art documents described hereinbefore, can also be applied in an analogous manner to oxamyl in the crystalline modification I of the invention.

Accordingly, the present invention provides an insecticide and nematicide composition comprising oxamyl in the crystalline modification I as defined hereinbefore.

The present invention furthermore provides processes for preparing compositions for controlling insect using the crystalline modification I of oxamyl.

The invention also provides a method for controlling insecticides and nematicides, comprising applying to the plant, plant part, or surroundings of the plant, a herbicidally effective amount of crystalline modification I of oxamyl according to any one of the first to seventh and ninth aspects of the invention, or a composition according to the tenth aspect of the invention. Accordingly, this provides for controlling insects and nematodes in plants, plant parts, and/or their surroundings, comprising applying to the foliage or fruit of the plant, plant part, or surroundings of the plant, an effective amount of crystalline modification I of oxamyl.

In an embodiment of the tenth aspect of the invention, the composition is in the form of a suspension concentrate (SC), soluble concentrate (SL), oil-based suspension concentrate (OD), water-soluble granule (SG), dispersible concentrate (DC), emulsifiable concentrate (EC), emulsion seed dressing, suspension seed dressing, granule (GR), microgranule (MG), suspoemulsion (SE) and water-dispersible granule (WG) using suitable auxiliaries, carriers and solvents.

In an embodiment of the tenth aspect of the invention, the composition is in the form of a suspension concentrate (SC) and granule (GR).

In an embodiment of the tenth aspect of the invention, the crystalline modification I of oxamyl may be present in a concentration sufficient to achieve the required dosage when applied to plants or the loci thereof, desirably in a concentration of about 0.1 to about 75% by weight of the total mixture. The formulations are prepared, for example, by extending the crystalline modification I of oxamyl with water, solvents and carriers, using, if appropriate, emulsifiers and/or dispersants, and/or other auxiliaries.

These formulations are prepared by mixing the crystalline modification I of oxamyl with at least one auxiliary, for example, surfactants, liquid diluents, solid diluents, wetting agents, dispersants, thickening agents, antifreezing agents, biocides and any necessary adjuvants and other formulation ingredients.

Surfactants can be an emulsifier, dispersant or wetting agent of ionic or nonionic type. Examples which may be used include, but are not limited to, salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, or phosphoric esters of polyethoxylated phenols or alcohols.

Liquid diluents include, but are not limited to, water, N,N-dimethylmamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, water and alcohols such methanol, cyclohexanol, decanol, benzyl and tetrahydrofurfuryl alcohol and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum, calcium and zinc oxide and mixtures thereof.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates. Polyalkylene glycol ether is particularly useful for the composition of the invention.

Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Of note are compositions comprising up to 10% by weight of dispersant. Ligninsulfonates such as sodium lignin-sulfonates are particularly useful for the composition of the invention. Sodium alkyl naphthalene sulfonate-formaldehyde condensate is particularly useful for the composition of the invention.

Thickening agents include, but are not limited to, guar gum, pectin, casein, carrageenan, xanthan gum, alginates, methylcellulose, hydroxyethylcellulose, hydroxypropylcellulose, and carboxymethylcellulose. Synthetic thickeners include derivatives of the former categories, and also polyvinyl alcohols, polyacrylamides, polyvinylpyrrolidones, various polyethers, their copolymers as well as polyacrylic acids and their salts. Xanthan gum is particularly useful for the composition of the invention.

Suitable antifreezing agents are liquid polyols, for example ethylene glycol, propylene glycol or glycerol. The amount of antifreeze agents is generally from about 1% to about 20% by weight, in particular from about 5 to about 10% by weight, based on the total weight of the composition.

Biocides may also be added to the composition according to the invention. Suitable Biocides are those based on isothiazolones, for example Proxel® from ICI or Acticide® RS from Thor Chemie or Kathon® MK from Rohm & Haas. The amount of biocides is typically from 0.05% to 0.5% by weight, based on the total weight of composition.

Antifoaming agents include all substances which can normally be used for this purpose in agrochemical compositions. Suitable anti-foam agents are known in the art and are available commercially. Particularly preferred antifoam agents are mixtures of polydimethylsiloxanes and perfluroalkylphosphonic acids, such as the silicone antifoaming agents available from GE or Compton.

Antioxidants include all substances which can normally be used for this purpose in agrochemical compositions, as is known in the art. Preference is given to butylated hydroxytoluene (BHT).

Other formulation ingredients can also be used in the present invention, such as dyes, drying agents, and the like. These ingredients are known to one skilled in the art.

In an embodiment of the tenth aspect of the invention, the crystalline modification I of oxamyl according to the invention can be present in its commercially available formulations and in its use forms, prepared from these formulations, and as a mixture with other active compounds, such as insecticides, attractants, sterilizing agents, bactericides, acaricides, nematicides, fungicides, growth-regulating substances, herbicides, safeners, fertilizers and semiochemicals.

All plants and plant parts can be treated in accordance with the invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown.

"Precipitation" as used herein, refers to the sedimentation of a solid material (a precipitate), including the sedimentation of a crystalline material, from a liquid solution in which the solid material is present in amounts greater than its solubility in the amount of liquid solution.

Treatment according to the invention of the plants and plant parts with the compositions or formulations of the inventions is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the invention are seen most when the composition is applied to kill insects and nematodes, such as Boll weevil, Flea hopper, Tarnished plant bug, Cotton leaf perforator, Pink bollworm, Aphids, Flea beetle, Potato leafhopper, Tarnished plant bug and Citrus thrips, in growing crops of useful plants: such as cotton, potato, ornamentals, fruit trees, vegetables, cucurbits, beet, bananas, apples, carrots, celery, citrus, pineapples, peanuts, soy beans, tobacco. In this invention, treatment of cotton and potato are particularly beneficial.

Throughout the description and claims of this specification, the words "comprise" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property then a range of values defined by a combination of any of the upper limits with any of the lower limits may also be implied.

In this specification, references to properties are unless stated otherwise to properties measured under ambient conditions, i.e. at atmospheric pressure and at a temperature of about 20° C.

The term "crystalline", as used herein, refers to a solid state form wherein molecules are arranged to form a crystal lattice comprising distinguishable unit cells. In general, crystalline material may, for example, be identified by yielding diffraction peaks when subjected to X-ray radiation and/or exhibiting an endothermic melting peak profile with a characteristic sharp peak under differential scanning calorimetry (DSC).

All percentages are given in weight % unless otherwise indicated.

BRIEF DESCRIPTION OF DRAWINGS

Various features and aspects of the embodiments of the invention disclosed herein can be more clearly understood by reference to the drawings, which are intended to exemplify and illustrate, but not to limit, the scope of the invention, and wherein.

DETAILED DESCRIPTION

The present invention will now be described by the following examples, and in which the following measurement techniques have been employed, and which the examples are provided for illustrative purposes only, and not intended to limit the scope of the disclosure.

Figure 1:
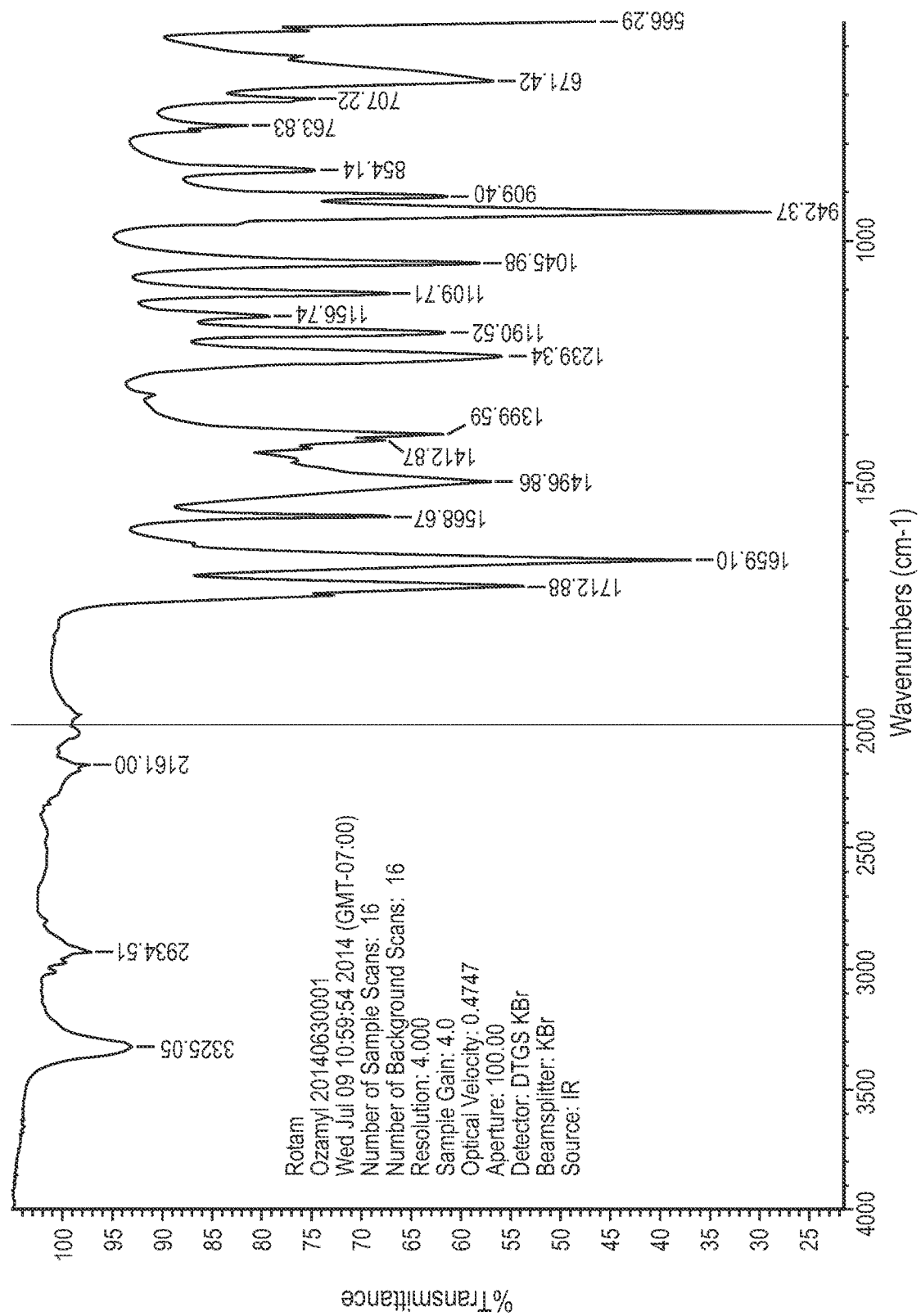
FIG. 1 is an infrared (IR) spectrum of an embodiment of crystalline modification I of oxamyl.

All X-ray diffractograms were determined using powder diffractometer in reflection geometry at 25° C., using the following acquisition parameters:

X'Pert Pro MPD from PANalytical B.V.
Theta compensating slit and graphite monochromator
Copper (K-alpha) radiation, 40 kV, 40 mA
Step size: 0.03 degree 2-theta
Count time: 1.0 second
Maximum peak intensity: 1705 counts per second
Scan range: 3-60 degrees 2-theta The IR spectrum was measured with the resolution of 4 cm$^{-1}$ and with the number of scans of 16 for the crystallized samples. The crystalline modification I of oxamyl can be identified by its characteristic functional group vibration peaks at wavenumbers (cm$^{-1}$, ±0.2%) of one or more of 3325.05, 2934.51, 2161.00, 1712.88 and 1659.10 cm$^{-1}$ as shown in FIG. 1.

All IR spectra were obtained using the following acquisition parameters:

| FT-IR spectrometer | Nicolet™ iS 5 |
| Diamond ATR unit | Thermo Scientific™ iD5 ATR |
| Wavelength range | 550-4000 cm$^{-1}$ |
| Resolution | 4 cm$^{-1}$ |
| Number of scans | 16 |

All DSC thermograms were obtained using the following acquisition parameters:

| Differential Scanning Calorimeter | DSC 214 Polyma from NETZSCH-Gerätebau GmbH |
| Range | 60° C./1.0 (K/min)/160° C. |
| Sample car./TC | DSC 214 Corona sensor/E |
| Segments | 1/1 |
| Crucible | Pan Al, closed |
| Atmosphere | N$_2$, 50.0 ml/min/N$_2$, 70.0 ml/min |
| Corr/m. range | 000/5000 µV |

EXAMPLES

Example 1: Preparation of Amorphous Oxamyl in Accordance with the Disclosure of U.S. Pat. No. 5,284,962, Example 2

A two-stage, co-currently fed, continuous reactor system was used to react MIC (methyl isocyanate) and the oxime, methyl 2-(dimethylamino)-N-hydroxy-2-oxoethanimidothioate, to produce methyl 2-(dimethylamino)-N-[[(methylamino)carbonyl]oxy]-2-oxoethanimidothioate (oxamyl). The reactors were maintained at approximately 42° C. During steady state operation, methyl isocyanate (MIC) was fed at a rate of 1.2 g/min and vaporized and mixed with nitrogen which was fed at approximately 2200 mL/min. The oxime was fed at a rate of 7.9 g/min as a 40% slurry in water containing 0.2% TEA. Conversion of the oxime in the first reactor was about 93%. The composition of the product solution from the second reactor was approximately 47% title product, 0.9% oxime and 0.8% DMU (dimethyl urea). This composition corresponded to 97% conversion of the oxime and 8% of the original MIC as DMU. The vent stream from the second reactor contained about 0.2% MIC corresponding to removal of greater than 99% from the gas stream.

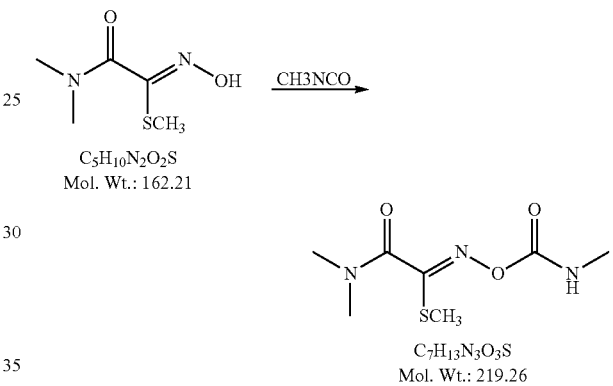

Scheme 1. Synthesis of oxamyl

Figure 4:
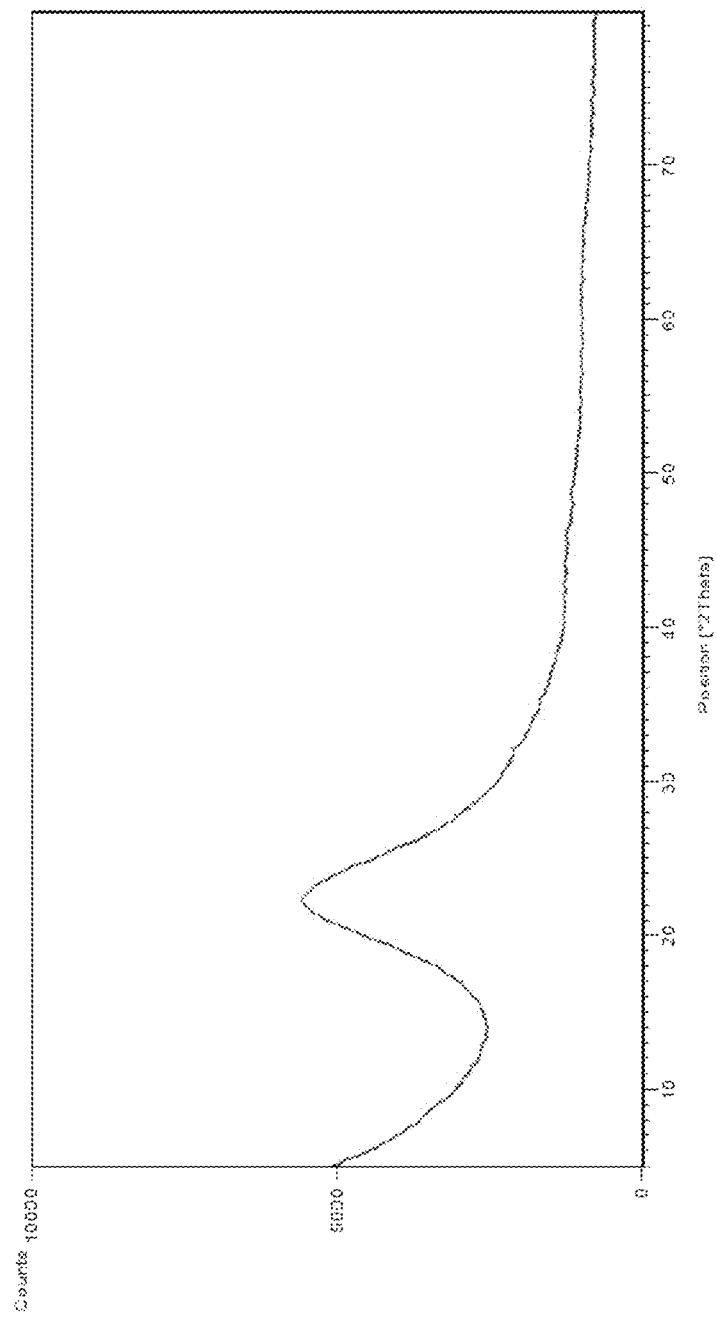
FIG. 4 is a X-ray powder diffractogram of amorphous oxamyl.

As shown in FIG. 4, the X-ray powder diffraction pattern of the resulting oxamyl product has no significant signals, which indicates the oxamyl product prepared in accordance with the disclosure of U.S. Pat. No. 5,284,962 is amorphous.

Example 2: Preparation of the Crystalline Modification I of Oxamyl

Crystallization from Ethyl Acetate 10 g of amorphous oxamyl sample prepared in Example 1 was taken in a 3 neck round bottom flask along with 50 mL of ethyl acetate and the resulting slurry was heated to 65° C. to get a homogeneous solution. The insoluble particles, if any, were filtered and the solution was slowly cooled to 20~25° C. Upon cooling, fine crystals were formed and the resulting heterogeneous mixture was stirred at 20° C. for 2 h. Then, the slurry was filtered and washed with 3 mL of ethyl acetate at 20° C. The filtered crystals were dried under vacuum at 40° C. The crystal product obtained had a purity of >98% and the recovered product as crystal was found to be about 90% yield.

Figure 2:
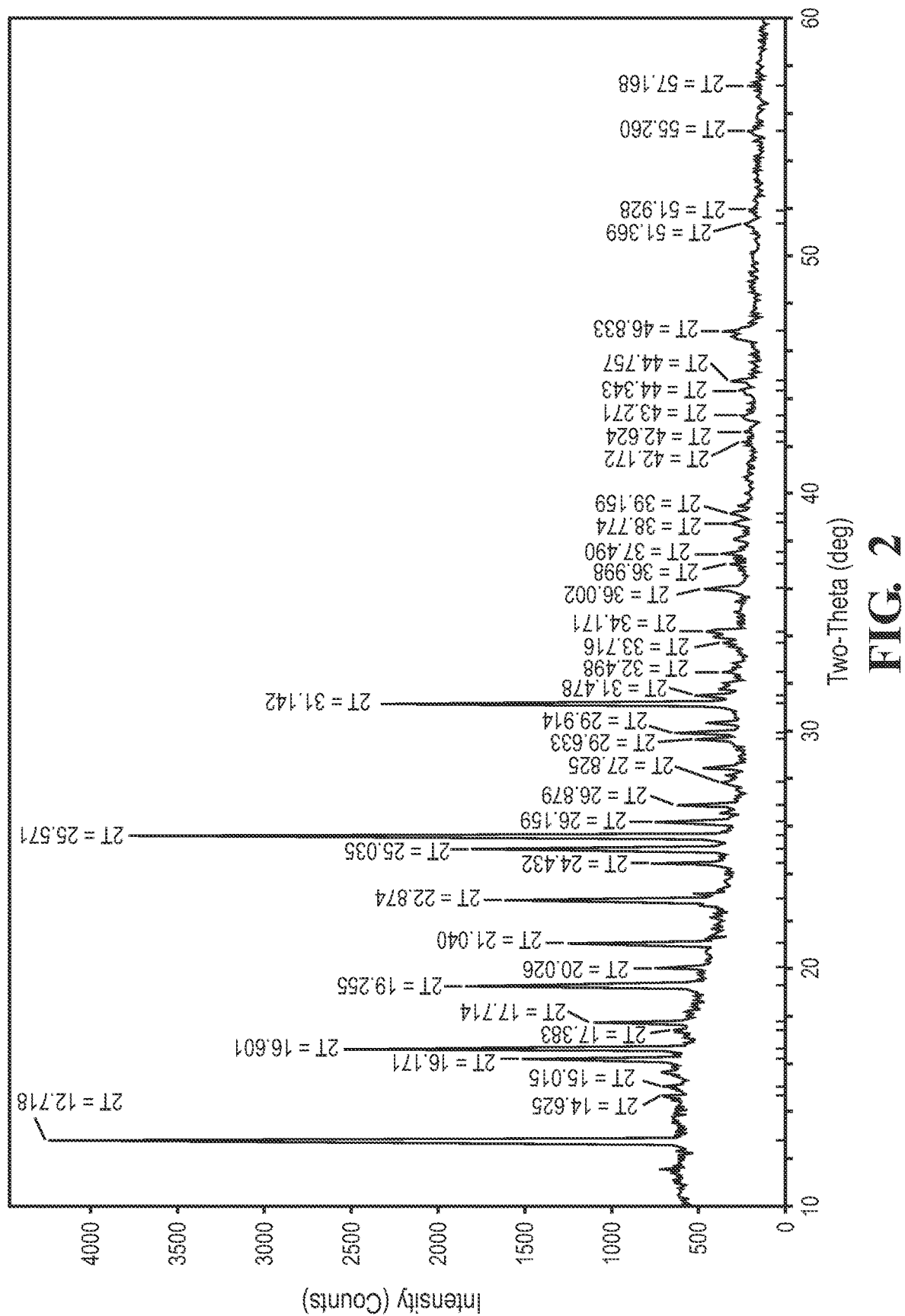
FIG. 2 is a X-ray powder diffractogram (X-RPD) of the crystalline modification I of oxamyl.
Figure 3:
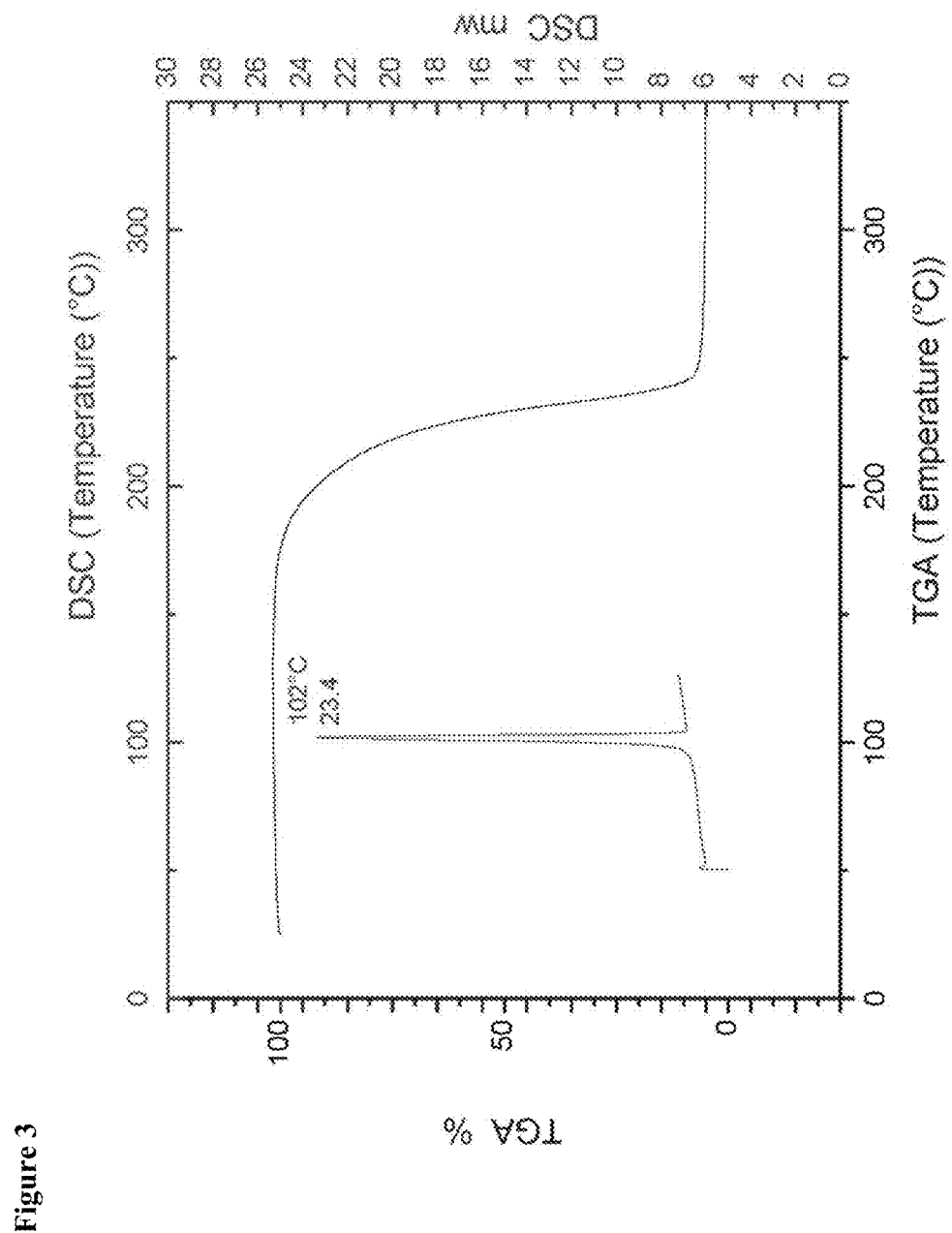
FIG. 3 is a Differential Scanning calorimetry (DSC) thermogram of crystalline modification I of oxamyl.

The obtained crystals were analyzed by IR spectrometry, X-RPD and DSC and found out to be crystalline modification I of oxamyl as shown in FIG. 1, FIG. 2 and FIG. 3, respectively.

The IR spectrum of the crystalline modification I of oxamyl is set out in FIG. 1. The IR spectrum of oxamyl exhibited the functional group characteristic vibrations peaks at wavenumbers of one or more of 3325.05, 2934.51, 2161.00, 1712.88 and 1659.10 cm$^{-1}$.

The DSC thermogram of oxamyl exhibited an endothermic melting peak at 102° C. as shown in FIG. 3.

The X-ray powder diffractogram of the crystals exhibited the reflexes in FIG. 2 and the values are summarized in Table 1.

TABLE 1

Crystalline Modification I

| 2θ(°) | d(Å) |
|---|---|
| 12.718 ± 0.2 | 8.076 ± 0.05 |
| 16.171 ± 0.2 | 6.360 ± 0.05 |
| 16.601 ± 0.2 | 6.196 ± 0.05 |
| 17.714 ± 0.2 | 5.809 ± 0.05 |
| 19.255 ± 0.2 | 5.349 ± 0.05 |
| 20.026 ± 0.2 | 5.145 ± 0.05 |
| 21.040 ± 0.2 | 4.899 ± 0.05 |
| 22.874 ± 0.2 | 4.511 ± 0.05 |
| 24.432 ± 0.2 | 4.227 ± 0.05 |
| 25.035 ± 0.2 | 4.127 ± 0.05 |
| 25.571 ± 0.2 | 4.042 ± 0.05 |
| 26.159 ± 0.2 | 3.953 ± 0.05 |
| 26.879 ± 0.2 | 3.849 ± 0.05 |
| 29.633 ± 0.2 | 3.498 ± 0.05 |
| 29.914 ± 0.2 | 3.466 ± 0.05 |
| 31.142 ± 0.2 | 3.332 ± 0.05 |

Example 3: Preparation of the Crystalline Modification I of Oxamyl

Crystallization from Nitrobenzene 5 g of amorphous oxamyl sample prepared in Example 1 was taken in a 3 neck round bottom flask along with 30 mL of nitrobenzene and the resulting slurry was heated to 83° C. to get a homogeneous solution. The insoluble particles, if any, were filtered and the solution was slowly cooled to 20° C. Upon cooling, fine crystals were formed and the resulting heterogeneous mixture was stirred at 20° C. for 2 h. Then, the slurry was filtered, washed with 3 mL of nitrobenzene at 20° C. and dried under vacuum at 45° C. The crystal product thus obtained had a purity of >98% and the recovered yield was found to be about 90% yield.

The crystals were characterized as being oxamyl crystalline modification I using IR spectrometry, X-ray powder diffraction and DSC, as described in Example 2.

Formulation Examples

Example 4 Preparation of Suspension Concentrate (SC), 42% Oxamyl

All the components list in Table 2 below were mixed uniformly and the resulting mixture was ground with a Dyno-Mill (manufactured by Willy A. Bachofen AG) to obtain a suspension concentrate.

TABLE 2

| | Weights % | | |
|---|---|---|---|
| Ingredients | Sample A | Comparative Sample A | Function |
| Oxamyl, crystalline modification I, 98% (prepared in Example 2) | 42.86 | 0 | Active compound |
| Amorphous oxamyl (prepared in Example 1) | 0 | 42.86 | Active compound |
| Propylene glycol | 5 | 5 | Anti-freezing agent |
| Modified polydimethylsiloxane formulation (SAG 1529) | 0.5 | 0.5 | Antifoaming agent |
| Sodium Alkylnaphthalenesulfonate, formaldehyde condensate (MORWET D-425 ® POWDER) | 3 | 3 | Dispersing agent |
| Polyalkylene glycol ether (ATLAS ™ G-5000) | 2 | 2 | Wetting agent |
| Xanthan gum (AG-RHO POL 23/W) | 0.2 | 0.2 | Thickening agent |
| 1,2-Benzisothiazol-3-one (NIPACIDE BIT 20) | 0.2 | 0.2 | Biocide |
| Water | Balance to 100% | Balance to 100% | Diluent |

Example 5 Preparation of Suspension Concentrate (SC) 24% Oxamyl

All the components list in Table 3 below were mixed uniformly and the resulting mixture was ground with a Dyno-Mill (manufactured by Willy A. Bachofen AG) to obtain a suspension concentrate.

TABLE 3

| | Weights % | | |
|---|---|---|---|
| Ingredients | Sample B | Comparative Sample B | Function |
| Oxamyl, crystalline modification I, 98% (prepared in Example 2) | 24.49 | 0 | Active compound |
| Amorphous oxamyl (prepared in Example 1) | 0 | 24.49 | Active compound |
| Propylene glycol | 5 | 5 | Anti-freezing agent |
| Modified polydimethylsiloxane formulation (SAG 1529) | 0.5 | 0.5 | Antifoaming agent |
| Sodium Alkylnaphthalenesulfonate, formaldehyde condensate (MORWET D-425 ® POWDER) | 3 | 3 | Dispersing agent |
| Polyalkylene glycol ether (ATLAS ™ G-5000) | 2 | 2 | Wetting agent |
| Xanthan gum (AG-RHO POL 23/W) | 0.2 | 0.2 | Thickening agent |
| 1,2-Benzisothiazol-3-one (NIPACIDE BIT 20) | 0.2 | 0.2 | Biocide |
| Water | Balance to 100% | Balance to 100% | Diluent |

Example 6: Preparation of Granules (GR), 10% Oxamyl

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm~2 mm screens to obtain the product granules.

TABLE 4

| Ingredients | Weights % Sample C | Comparative Sample C | Function |
|---|---|---|---|
| Oxamyl, crystalline modification I, 98% (prepared in Example 2) | 10.2 | 0 | Active compound |
| Amorphous oxamyl (prepared in Example 1) | 0 | 10.2 | Active compound |
| Alkyl naphthalene sulphonate, sodium salt (Akzo Nobel) | 1.6 | 1.6 | Wetting agent |
| Lignosulfonic acid, sodium salt (REAX ® 88B) | 8 | 8 | Dispersing agent |
| Fatty acids, tallow, sodium salts (AGNIQUE ® SOAP L) | 1 | 1 | Antifoaming agent |
| Mannitol (Shangdong Tianli) | Balance to 100% | Balance to 100% | Filler |

Example 7: Comparison of the Storage Stability

Samples prepared in Examples 4, 5 and 6 were stored in heated ovens (54° C.) having the same atmosphere for 1 month, 3 months and 6 months. The procedures are followed according to CIPAC MT 46.3. The concentration of oxamyl was tested at the end of each storage time by high pressure liquid chromatography (HPLC). The aggregation was measured by observation. The results are listed in Table 5.

TABLE 5

| Sample | Formulation | Original concentration, % | 1 month Concentration of oxamyl (%) | 1 month Aggregation | 3 month Concentration of oxamyl (%) | 3 month Aggregation | 6 month Concentration of oxamyl (%) | 6 month Aggregation |
|---|---|---|---|---|---|---|---|---|
| Sample A | SC | 42 | 42 | − | 42 | − | 42 | − |
| Comparative Sample A | SC | 42 | 38 | ++ | 31 | +++ | 20 | +++++ |
| Sample B | SC | 24 | 24 | − | 24 | − | 24 | − |
| Comparative Sample B | SC | 24 | 20 | ++ | 15 | +++ | 10 | +++++ |
| Sample C | GR | 10 | 10 | − | 10 | − | 10 | − |
| Comparative Sample C | GR | 10 | 9 | + | 8 | ++ | 5 | +++ |

Remark: "+" means small amount of aggregation.
"+++++" means a lot of aggregation.
"−" means no aggregation.

The invention claimed is:

1. A crystalline modification I of (EZ)-N,N-dimethyl-2-methylcarbamoyloxyimino-2-(methylthio)acetamide (oxamyl), exhibiting the following reflexes, as 2θ±0.20 degree in X-ray powder diffractogram (X-RPD) recorded using Cu-Kα radiation at 25° C.:

$$2\theta = 12.72 \pm 0.20 \tag{1}$$

$$2\theta = 16.17 \pm 0.20 \tag{2}$$

$$2\theta = 16.60 \pm 0.20 \tag{3}$$

$$2\theta = 19.26 \pm 0.20 \tag{5}$$

$$2\theta = 21.04 \pm 0.20 \tag{7}$$

$$2\theta = 22.87 \pm 0.20 \tag{8}$$

$$2\theta = 25.04 \pm 0.20 \tag{10}$$

$$2\theta = 25.57 \pm 0.20 \tag{11}$$

$$2\theta = 31.14 \pm 0.20 \tag{16}.$$

2. The crystalline modification I of oxamyl according to claim 1, exhibiting an IR spectrum with characteristic functional group vibration peaks at wavenumbers (cm$^{-1}$, ±0.2%) of one or more of about 3325, 2935, 2161, 1713 and 1659 cm$^{-1}$.

3. The crystalline modification I of oxamyl according to claim 1, exhibiting a melting point of 100° C. to 104° C.

4. The crystalline modification I of oxamyl according to claim 1, exhibiting a differential scanning calorimetry (DSC) profile having an endothermic melting peak at 102° C.

5. A process for the preparation of a crystalline modification I of oxamyl according to claim 1, comprising:
   i) dissolving oxamyl in a solvent, or mixture of solvents;
   ii) precipitating the dissolved compound into crystalline modification I of oxamyl; and
   iii) isolating the precipitated crystalline modification I.

6. The process according to claim 5, where the oxamyl in step i) is amorphous oxamyl.

7. The process according to claim 5, wherein the solvent is selected from the group consisting of nitrobenzene, toluene, xylene, chlorobenzene, dichlorobenzene, trifluoro methyl benzene, mesitylene, ether, ethyl acetate or a mixtures thereof.

8. The process according to claim 5, where the solvent is selected from the group consisting of ethyl acetate and/or nitrobenzene or a mixture thereof.

9. The process according to claim 5, wherein step ii) comprises concentrating the solution and/or by cooling and/or by the addition of a solubility reducing solvent and/or by adding a seed crystal of the crystalline modification I of oxamyl.

10. The process according to claim 9, wherein step ii) is effected by cooling to about 0° C. to 20° C.

11. The crystalline modification I of oxamyl according to claim 1, obtainable by the process of
   i) dissolving oxamyl in a solvent, or mixture of solvents;
   ii) precipitating the dissolved compound into crystalline modification I of oxamyl; and
   iii) isolating the precipitated crystalline modification I.

12. A crystalline modification I of oxamyl obtained by a process according to claim 5 and having a content of crystalline modification I of oxamyl of at least 98% by weight.

13. A composition comprising the crystalline modification I of oxamyl according to claim 1 and at least one auxiliary.

14. The composition according to claim 13, wherein the auxiliary is selected from one or more of a surfactant, a liquid diluent, a solid diluent, a wetting agent, a dispersant, a thickening agent, an antifreezing agent and a biocide.

15. The composition according to claim 14, wherein the other formulation ingredients can be are dyes and drying agents.

16. The composition according to claim 13, which is in form of a suspension concentrate (SC), an oil-based suspension concentrate (OD), an soluble concentrate (SL), a water-soluble granule (SG), a dispersible concentrate (DC), an emulsifiable concentrate (EC), an emulsion seed dressing, a suspension seed dressing, a granule (GR), a microgranule (MG), a suspoemulsion (SE) or a water-dispersible granule (WG).

17. The composition according to claim 16, which is in form of a suspension concentrate (SC) or a granule (GR).

18. The composition according to claim 13, which comprises crystalline modification I of oxamyl in an amount of less than 75% by weight.

19. The composition according to claim 13, which comprises crystalline modification I of oxamyl in an amount of 42% by weight.

20. The composition according to claim 13, which comprises crystalline modification I of oxamyl in an amount of 24% by weight.

21. The composition according to claim 13, which comprises crystalline modification I of oxamyl in an amount of 10% by weight.

22. A method for the control of insects and nematodes, comprising applying the crystalline modification I of oxamyl according to claim 1 to a plant, a plant part, or surroundings of a plant.

23. The method according to claim 22, wherein the insects and nematodes are selected from the group consisting of Boll weevil, Flea hopper, Tarnished plant bug, Cotton leaf perforator, Pink bollworm, Aphids, Flea beetle, Potato leafhopper, Tarnished plant bug and Citrus thrips.

24. The method according to claim 22, wherein the insects and nematodes are insects and nematodes on cotton and potato.

25. The crystalline modification I of oxamyl according to claim 1, characterized by X-ray powder diffraction pattern as shown in FIG. 2, and/or characterized by an IR spectrum as shown in FIG. 1, and/or characterized by a DSC thermogram as shown in FIG. 3.

* * * * *